United States Patent
Mori et al.

(10) Patent No.: US 10,542,651 B2
(45) Date of Patent: Jan. 21, 2020

(54) INSPECTION APPARATUS AND QUALITY CONTROL SYSTEM FOR SURFACE MOUNTING LINE

(71) Applicant: OMRON Corporation, Kyoto-shi, Kyoto (JP)

(72) Inventors: Hiroyuki Mori, Ono (JP); Mayuko Kishimoto, Kyoto (JP); Shimpei Fujii, Souraku-gun (JP); Katsuki Nakajima, Kyoto (JP)

(73) Assignee: OMRON Corporation, Kyoto-shi (JP)

( * ) Notice: Subject to any disclaimer, the term of this patent is extended or adjusted under 35 U.S.C. 154(b) by 114 days.

(21) Appl. No.: 15/653,667

(22) Filed: Jul. 19, 2017

(65) Prior Publication Data
US 2018/0049356 A1    Feb. 15, 2018

(30) Foreign Application Priority Data

Aug. 10, 2016   (JP) ................... 2016-157876

(51) Int. Cl.
*H05K 13/08*        (2006.01)
*G01N 21/956*     (2006.01)
(Continued)

(52) U.S. Cl.
CPC ........... *H05K 13/08* (2013.01); *B23K 1/0016* (2013.01); *B23K 3/08* (2013.01);
(Continued)

(58) Field of Classification Search
None
See application file for complete search history.

(56) References Cited

U.S. PATENT DOCUMENTS

2003/0053714 A1*   3/2003   Esaki ................... G06K 9/4604
                                                                        382/287
2003/0174877 A1*   9/2003   Aiger ............... G01N 21/95684
                                                                        382/145
(Continued)

FOREIGN PATENT DOCUMENTS

CN          202841832 U       3/2013
CN          202841833 U       3/2013
(Continued)

OTHER PUBLICATIONS

Office action dated Jun. 24, 2019, in a counterpart Chinese patent application.

*Primary Examiner* — Mekonen T Bekele
*Assistant Examiner* — Nathan J Bloom
(74) *Attorney, Agent, or Firm* — Metrolex IP Law Group, PLLC

(57) ABSTRACT

An inspection apparatus includes an imaging unit that captures an image of a board having a land on which a solder piece has been printed, an image of the board having a component mounted on the solder piece, or an image of the board having the component soldered to the land, a land determination unit that determines a position of an element on the board other than the land from the image of the board captured by the imaging unit, and determines a position of the land in the image based on the determined position of the element, and an inspection unit that inspects the solder piece or component on the land using the position of the land determined by the land determination unit as a reference.

17 Claims, 12 Drawing Sheets

(51) Int. Cl.
  *G06T 7/00*     (2017.01)
  *G06T 7/73*     (2017.01)
  *B23K 1/00*     (2006.01)
  *B23K 3/08*     (2006.01)
  *G05B 19/418*   (2006.01)
  *H05K 1/02*     (2006.01)
  *H05K 3/34*     (2006.01)
  *B23K 101/42*   (2006.01)
  *G01R 31/04*    (2006.01)

(52) U.S. Cl.
  CPC . *G01N 21/95684* (2013.01); *G05B 19/41875* (2013.01); *G06T 7/001* (2013.01); *G06T 7/74* (2017.01); *H05K 1/0269* (2013.01); *H05K 3/341* (2013.01); *H05K 13/0817* (2018.08); *B23K 2101/42* (2018.08); *G01R 31/048* (2013.01); *G06T 2207/30141* (2013.01); *H05K 2203/163* (2013.01)

(56) References Cited

U.S. PATENT DOCUMENTS

| | | | |
|---|---|---|---|
| 2004/0218808 A1* | 11/2004 | Prince | B23K 3/08 |
| | | | 382/150 |
| 2012/0060357 A1* | 3/2012 | Kaida | H05K 13/0413 |
| | | | 29/593 |
| 2013/0087057 A1* | 4/2013 | Kondo | H05K 3/1233 |
| | | | 101/123 |
| 2014/0373346 A1* | 12/2014 | Okamoto | H05K 3/1233 |
| | | | 29/825 |

FOREIGN PATENT DOCUMENTS

| | | |
|---|---|---|
| CN | 202841834 U | 3/2013 |
| JP | H09-186444 A | 7/1997 |
| JP | 2002-271096 A | 9/2002 |

* cited by examiner

Component deviation (Y)

Component deviation (X)

Distance between electrode front end and land front end

Solder wetting angle

FIG. 9

| Board ID | Item No. | Post-solder printing inspection | | | Post-mount inspection | | | Post-reflow inspection | | | Visual inspection |
|---|---|---|---|---|---|---|---|---|---|---|---|
| | | Measurement value | | Inspection result | Measurement value | | Inspection result | Measurement value | | Inspection result | |
| | | Solder deviation | ... | | Component deviation | ... | | Component deviation | ... | | |
| B001 | P01 | X:0, Y:3 | ... | Pass | X:1, Y:1 | ... | Pass | X:1, Y:2 | ... | Pass | Acceptable |
| B001 | P02 | X:0, Y:3 | ... | Pass | X:1, Y:0 | ... | Pass | X:0, Y:2 | ... | Pass | Acceptable |
| B001 | P03 | X:-5, Y:3 | ... | Fail (Deviation in X-direction) | X:-4, Y:1 | ... | Fail (Deviation in X-direction) | X:-5, Y:2 | ... | Fail (Deviation in X-direction) | Defective |
| ... | ... | ... | ... | ... | ... | ... | ... | ... | ... | ... | ... |
| B001 | P15 | X:-1, Y:2 | ... | Pass | X:0, Y:1 | ... | Pass | X:0, Y:1 | ... | Pass | Acceptable |
| B002 | P01 | X:-1, Y:3 | ... | Pass | X:0, Y:6 | ... | Fail (Deviation in Y-direction) | X:0, Y:3 | ... | Pass | Acceptable |
| ... | ... | ... | ... | ... | ... | ... | ... | ... | ... | ... | ... |

| Board ID | Item No. | Nozzle No. | Nozzle ID | Feeder ID | Head ID | ... |
|---|---|---|---|---|---|---|
| B001 | P01 | 1 | N001 | F001 | H005 | ... |
| B001 | P02 | 2 | N002 | F002 | H005 | ... |
| B001 | P03 | 5 | N003 | F003 | H005 | ... |
| ... | ... | ... | ... | ... | ... | ... |
| B001 | P15 | 2 | N002 | F015 | H005 | ... |
| B002 | P01 | 1 | N001 | F001 | H005 | ... |
| ... | ... | ... | ... | ... | ... | ... |

FIG. 12

| Nozzle ID | Possible cause? | Number of defects | Defect rate | Odds ratio | Odds ratio 95% confidence interval lower limit |
|---|---|---|---|---|---|
| N001 | No | 1 | 0.0004 | 0.5 | 0.0 |
| N002 | Yes | 46 | 0.0032 | 4.7 | 3.9 |
| N003 | No | 7 | 0.0009 | 0.9 | 0.2 |

FIG. 13

| Nozzle ID | Possible cause? | Cpk | Cpk 95% confidence interval lower limit |
|---|---|---|---|
| N001 | No | 1.57 | 1.43 |
| N002 | Yes | 1.26 | 1.19 |
| N003 | No | 1.42 | 1.37 |

FIG. 14

| | | |
|---|---|---|
| Defect location | Time | 2016.6.30 10:23:36 |
| | Board ID | B001 |
| | Mounting surface | Front |
| Cause part | Cause type | Nozzle |
| | Cause ID | N001 |
| Operating site at defect occurrence | Line name | SMT5 |
| | Apparatus type | Mounter |
| | Apparatus name | MNT-0002 |
| | Nozzle No. | 12 |
| Current operating site | Line name | SMT3 |
| | Apparatus type | Mounter |
| | Apparatus name | MNT-0001 |
| | Nozzle No. | 16 |

INSPECTION APPARATUS AND QUALITY CONTROL SYSTEM FOR SURFACE MOUNTING LINE

CROSS REFERENCE TO RELATED APPLICATIONS

This application claims priority from prior Japanese Patent Application No. 2016-157876 filed with the Japan Patent Office on Aug. 10, 2016, the entire contents of which are incorporated herein by reference.

FIELD

The disclosure relates to inspection and quality control performed in a surface mounting line.

BACKGROUND

A surface mounting line includes a solder printing process in which pasty solder is printed onto electrode areas (lands) on a printed board, a mounting process in which electronic components are mounted on the solder, and a reflow process in which the board is heated in a reflow furnace to melt the solder and join the components to the board. An automated and labor-saving production line includes an inspection apparatus installed at the end of each process to perform an automated inspection using imaging (refer to, for example, Patent Literature 1).

CITATION LIST

Patent Literature

Patent Literature 1: Japanese Unexamined Patent Application Publication No. 2002-271096

SUMMARY

Technical Problem

Each process includes a positional deviation inspection, which is one important item of inspection. For example, the inspection after solder printing includes an inspection for determining whether a solder piece has been printed on its correct position. The inspection after mounting and the inspection after the reflow process each include an inspection for determining whether the component has been placed on its correct position. Inspection apparatuses known in the art typically use a design value (theoretical value) as the correct position, which serves as a reference. More specifically, a fiducial mark is used as a reference in positioning a circuit board. The coordinates of the position at which a solder piece or a component is to be placed are then calculated based on computer-aided design (CAD) data. A positional deviation of the solder piece or the component is then evaluated using the coordinates as a reference.

Such techniques using design values assume that a circuit board (or more specifically a land onto which a solder piece or a component is to be placed) has the size and positions exactly as designed. However, the actual land position may often deviate from its design value due to manufacturing errors, or strains and warps in the board. Further, the land is formed from a part of copper foil that is uncovered with a resist. This structure can have different uncovered areas for different wiring patterns to be connected to the land. The actual surface area or the shape of the land may often deviate from its design value. A positional deviation inspection using a design value based on CAD data as a reference, when performed for a land at a position deviating from its design value, can cause an erroneous determination, such as a false positive or a false negative.

Ideally, the actual land position on the circuit board is to be used as a reference, instead of the design value. However, determining the actual land position on the board during inspection in each process is difficult, because the land may be hidden almost entirely under a solder piece or a component and the outer shape of the land is unknown from the image of the board.

Patent Literature 1 above describes a technique for separating a land area from a solder area in a captured image of a board on which the solder piece has been printed, and interpolating the missing portion of the land area using preliminary prepared land data to restore the land area. This technique may yield reliable results for a land that largely deviates from a solder piece and appears mostly in the image (in other words, a land having a sufficiently small missing portion) as shown in FIG. 14 in Patent Literature 1. However, in an actual inspection, a land may typically be hidden almost entirely under a solder piece or a component. The technique proposed in Patent Literature 1 is thus inapplicable to many cases.

In response to the above issue, one or more aspects of the present invention are directed to a technique for an inspection using an actual land position as a reference in a surface mounting line.

Solution to Problem

In response to the above issue, the structure according to a first aspect of the present invention determines the position of an element other than a land, and then determines the position of the land using the position of the element as a reference.

More specifically, a first aspect of the preset invention provides an inspection apparatus for a surface mounting line. The apparatus includes an imaging unit that captures an image of a board having a land on which a solder piece has been printed, an image of the board having a component mounted on the solder piece, or an image of the board having the component soldered to the land, a land determination unit that determines a position of an element on the board other than the land from the image of the board captured by the imaging unit, and determines a position of the land included in the image based on the determined position of the element, and an inspection unit that inspects the solder piece or the component on the land using the position of the land determined by the land determination unit as a reference.

This structure determines the land position using the position of the element other than the land as a reference, and thus accurately determines the actual position of the land that may be hidden under a solder piece or a component. This structure then inspects the solder piece or the component using the actual land position as a reference, and thus allows more accurate determination than with techniques known in the art, and prevents false negatives for defective components, and improves the first pass yield.

The board having a land on which a solder piece has been printed refers to a board obtained after a solder printing process. The board having a component mounted on the solder piece refers to a board obtained after a component mounting process.

The board having the component soldered to the land refers to a board obtained after a reflow process. The inspection apparatus according to one or more aspects of the present invention can thus be used in any of a post-solder printing inspection, a post-mount inspection, and a post-reflow inspection. The element other than the land may be any element on the board that is substantially unlikely to be hidden under a solder piece or a component. The element may be, for example, a wiring pattern formed on the board.

In some embodiments, the land determination unit estimates the position of the land in the image based on positional relationship information defining a relative positional relationship between the element and the land, and the position of the element determined from the image. The positional relationship information is information generated by measuring a sample board on which no solder piece has been printed.

The positional relationship information may be information generated using a design value such as CAD data. However, the actual surface area or the shape of the land may deviate from its design value. The relative positional relationship between the element and the land may thus be determined more accurately using the positional relationship information generated from a measurement value of the actual sample board.

In some embodiments, the positional relationship information includes a template of the element generated from an image of the sample board. The land determination unit determines the position of the element in the image of the board by template matching using the template.

Despite any variation in the shape and the position of the element due to, for example, differences between individual boards, the template matching used to determine the position of the element allows simple and highly accurate determination of the element.

The structure according to a second aspect of the present invention provides a quality control system including the inspection apparatus according to the first aspect, and an analyzer that analyzes a cause of a defect or quality deterioration based on inspection data obtained by the inspection apparatus. The quality control system is expected to analyze the cause of the defect or the quality deterioration based on the inspection data using the actual land position as a reference.

The analyzer may correct a control parameter for a manufacturing apparatus included in the surface mounting line based on an analysis result of the cause of the defect or the quality deterioration. The analyzer may provide the analysis result of the cause of the defect or the quality deterioration to the manufacturing apparatus included in the surface mounting line. The analyzer can thus reduce defects and improve the quality.

The structure according to a third aspect of the present invention provides a quality control system including a first inspection apparatus that performs an intermediate inspection for a board having a land on which a solder piece has been printed, or for the board having a component mounted on the solder piece, a second inspection apparatus that performs a final inspection for inspecting the board having the component soldered to the land, and an analyzer. Each of the first and second inspection apparatuses is the inspection apparatus according to the first aspect of the present invention. The inspection unit included in each of the first and second inspection apparatuses compares a value measured using the position determined by the land determination unit as a reference with an inspection criterion to determine whether an inspection target is acceptable or defective. The analyzer changes a value of the inspection criterion used in the intermediate inspection based on a result of the determination performed in the final inspection. The analyzer may change the value of the inspection criterion used in the intermediate inspection to increase a degree of agreement between the result of the determination performed in the final inspection and a result of the determination performed in the intermediate inspection.

This structure allows the inspection criterion for intermediate inspections to be changed to appropriate values based on the determination results in the final inspection. This can minimize erroneous determinations of components that would not be defective after the reflow process as defective in the intermediate inspections (false positives) or erroneous determinations of components that would be defective after the reflow process as acceptable in the intermediate inspections (false negatives), and can reduce ineffective inspections. In this case as well, the quality control system performs the inspection using the actual land position as a reference, and optimizes the inspection criterion based on data obtained from the inspection. This structure is thus expected to enable more accurate and more reliable inspection.

The analyzer according to a fourth aspect of the present invention may generate and output, when an operating condition of the manufacturing apparatus and/or the inspection apparatus included in the surface mounting line is changed, information indicating a change in quality before and after the operating condition is changed. This structure allows easy and objective verification of the effects of any change in the operating conditions of the manufacturing apparatuses and/or the inspection apparatuses on the quality improvement. This can simplify the quality control of a surface mounting line and improve productivity.

The aspects of the present invention provide an inspection apparatus including at least some of the components or functions described above. The aspects of the present invention also provide a quality control system for performing the quality control of a surface mounting line based on inspection data obtained by the inspection apparatus. The aspects of the present invention also provide a method for controlling the inspection apparatus or an inspection method, a method for controlling a quality control system or a quality control method including at least some of the processes described above, a program enabling a computer (a processor) to implement the processes included in the method, or a computer-readable storage medium storing the program in a non-transitory manner. The processes and components described above may be combined when such combinations do not cause technical conflicts between them.

Advantageous Effects

Embodiments of the present invention may allow an inspection using an actual land position as a reference in a surface mounting line.

BRIEF DESCRIPTION OF THE DRAWINGS

FIG. 9 is a diagram showing an example of inspection data stored in an inspection database.

FIG. 12 is a diagram showing examples of analysis results provided to a mounter.

FIG. 13 is a diagram showing examples of analysis results obtained using the Cpk.

FIG. 14 is a diagram showing examples of analysis results provided to the mounter.

DETAILED DESCRIPTION

Embodiments of the present invention will now be described with reference to the drawings. The components described below may be modified in accordance with the system configuration or other conditions in the embodiments. The description herein does not intend to limit the scope of the present invention to the embodiments described below.

First Embodiment

System Configuration

Figure 1:
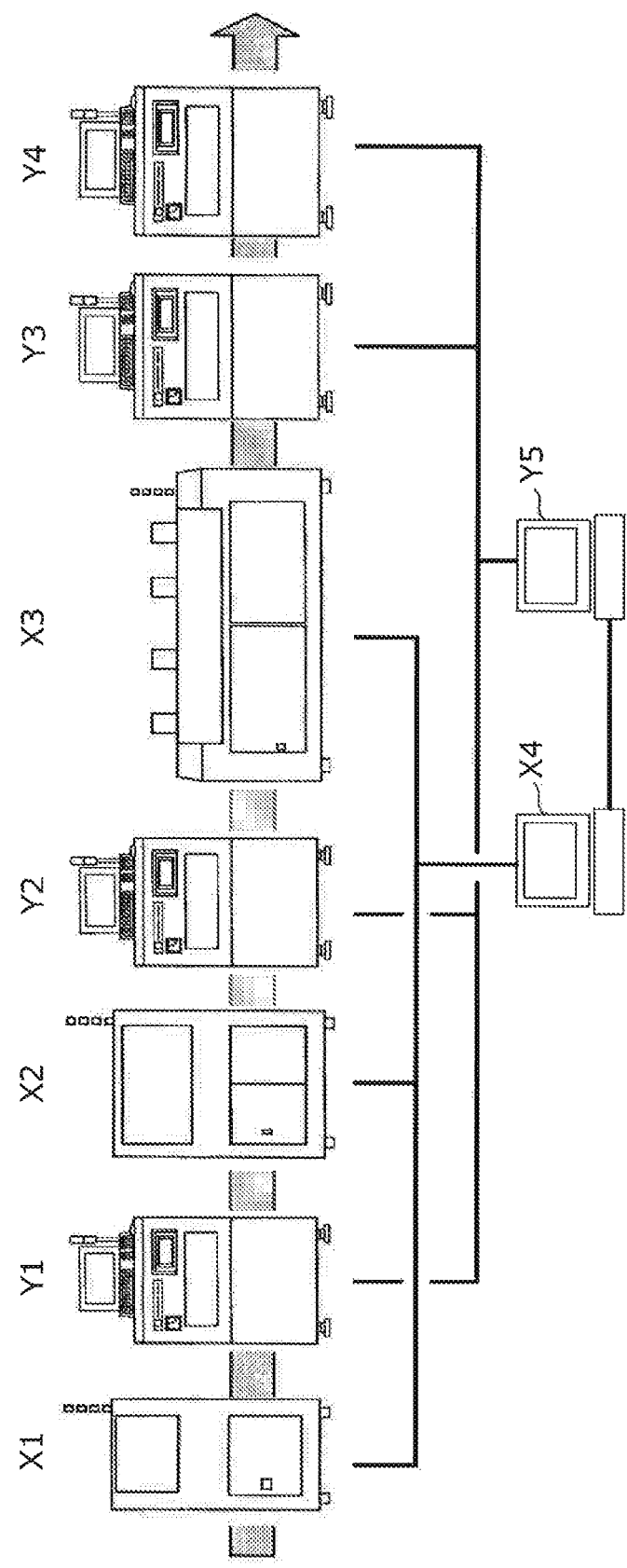
FIG. 1 is a diagram showing the configuration of a production system included in a surface mounting line.

FIG. 1 schematically shows the configuration of a production system included in a surface mounting line for printed boards in one embodiment. Surface-mount technology (SMT) is a method for soldering an electronic component onto the surface of a printed board. The surface mounting line includes three main processes, which are solder printing, component mounting, and reflow (solder melting).

As shown in FIG. 1, the surface mounting line includes manufacturing apparatuses including a solder printing apparatus X1, a mounter X2, and a reflow furnace X3 installed in this order from upstream. The solder printing apparatus X1 prints pasty solder onto electrode areas (lands) on a printed board by screen printing. The mounter X2, which is also called a chip mounter, picks up an electronic component to be mounted on the board, and places the component in the corresponding solder paste area. The reflow furnace X3 heats the solder paste to melt and then cools it to solder the electronic component onto the board. The surface mounting line may include multiple mounters X2 when a plurality of electronic components or different types of electronic components are mounted onto the board. A manufacture management apparatus X4 manages manufacturing apparatuses X1 to X3.

The surface mounting line also includes a quality control system for inspecting the state of the board at the end of each process of solder printing, component mounting, and reflow, and automatically detects a defect or quality deterioration (defect sign). In addition to such automated sorting of acceptable components and defective components, the quality control system improves the operations of the manufacturing apparatuses (by, for example, changing the control parameters) in accordance with the inspection results or their analysis results. As shown in FIG. 1, the quality control system of the present embodiment includes four inspection apparatuses, which are a solder printing inspection apparatus Y1, a component inspection apparatus Y2, an appearance inspection apparatus Y3, and an X-ray inspection apparatus Y4, and also an analyzer Y5.

The solder printing inspection apparatus Y1 inspects the state of the printed solder paste on the board fed from the solder printing apparatus X1. The solder printing inspection apparatus Y1 measures the solder paste printed on the board in a two-dimensional or three-dimensional manner, and determines whether various inspection items for the solder paste fall within the range of normal values (tolerances) based on the measurement results. The inspection items include the volume, the surface area, the height, the positional deviation, and the shape of the solder. The solder paste is two-dimensionally measured with, for example, an image sensor (camera), and three-dimensionally measured with, for example, a laser shift meter, a phase shifting method, a space-coding method, and a light-section method.

The component inspection apparatus Y2 inspects the arrangement of electronic components on the board fed from the mounter X2. The component inspection apparatus Y2 measures a component placed on the solder paste (which may be the component body or a part of the component such as an electrode, or a lead) in a two-dimensional or three-dimensional manner, and determines whether various inspection items for the component fall within the range of normal values (tolerances) based on the measurement results. The inspection items include a component positional deviation, a component angular (rotational) deviation, a missing component (no component being placed), a component mix-up (a different component being placed), different polarities (the polarity of the component different from the polarity of the board), a reversal (a component being placed upside down), and a component height. In the same manner as in the post-solder printing inspection, the electronic component is two-dimensionally measured with, for example, an image sensor (camera), and three-dimensionally measured with, for example, a laser shift meter, a phase shifting method, a space-coding method, and a light-section method.

The appearance inspection apparatus Y3 inspects the quality of solder joints on the board fed from the reflow furnace X3. The appearance inspection apparatus Y3 measures the post-reflow solder in a two-dimensional or three-dimensional manner, and determines whether various inspection items for the solder joints fall within the range of normal values (tolerances) based on the measurement results. The inspection items include the quality of a solder fillet shape in addition to the items used in a post-mount inspection. The shape of solder is determined with, for example, a laser shift meter, a phase shifting method, a space-coding method, and a light-section method described above, and also with the color highlight system (a method for detecting the three-dimensional shape of solder with two-dimensional hue information by illuminating the solder surface with RGB color light at different angles of incidence and capturing the reflected light of each color using a top camera).

The X-ray inspection apparatus Y4 inspects the state of solder joints on the board using an X-ray image. For example, a multilayer board and a package component, such as a ball grid array (BGA) and a chip size package (CSP), have solder joints hidden under the board or the component. In this case, the state of the solder cannot be inspected with the appearance inspection apparatus Y3 (or with an appearance image). The X-ray inspection apparatus Y4 overcomes such weakness of an appearance inspection. The inspection items of the X-ray inspection apparatus Y4 include a component positional deviation, a solder height, a solder volume, a solder ball diameter, a back fillet length, and the quality of a solder joint. The X-ray images may be images taken by projecting X-rays, or may be images taken using the computed tomography (CT) scan.

The above manufacturing apparatuses X1 to X3 are connected to the manufacture management apparatus X4 with a network. The manufacture management apparatus X4 is a system responsible for generating control programs for the manufacturing apparatuses X1 to X3, transmitting the control programs to the manufacturing apparatuses X1 to X3, and collecting log data from the manufacturing apparatuses X1 to X3. The inspection apparatuses Y1 to Y4 are connected to the analyzer Y5 with a network. The analyzer Y5 is a system responsible for generating inspection programs for the inspection apparatuses Y1 to Y4, transmitting the inspection programs to the inspection apparatuses Y1 to Y4, and collecting inspection data from the inspection apparatuses Y1 to Y4. The manufacture management apparatus X4 and the analyzer Y5 can exchange data between them with a network.

The control programs are data defining the operations of the manufacturing apparatuses X1 to X3, and includes information about manufacturing targets (e.g., board IDs, board sizes, and the item numbers, positions, and sizes of components) and control parameters (e.g., squeegee pressure, squeegee speed, printing pressure, and mask positions for the solder printing apparatus X1, the mounting positions of components, nozzle absorption pressure, and the pushed-in amount of the components for the mounter X2, and the temperature and the heating time for the reflow furnace X3).

The inspection programs are data defining the operations of the inspection apparatuses Y1 to Y4, and includes information about inspection targets (e.g., board IDs, board sizes, and the item numbers, positions, and sizes of components), information about inspection areas (e.g., the positions and sizes of inspection areas), and the inspection logic (e.g., measurement items, inspection items, and an inspection criterion).

The manufacture management apparatus X4 and the analyzer Y5 may both be general-purpose computer systems each including a central processing unit (CPU, or processor), a main storage unit (memory), an auxiliary storage unit (e.g., a hard disk drive), an input device (e.g., a keyboard, a mouse, a controller, and a touch panel), and a display. The functions of the manufacture management apparatus X4 and the analyzer Y5, which will be described later, are implemented by the CPU reading the programs stored in the auxiliary storage unit and executing the programs.

The manufacture management apparatus X4 and the analyzer Y5 may be implemented using a single computer or may be implemented using multiple computers. A computer included in any one of the manufacturing apparatuses X1 to X3 and the inspection apparatuses Y1 to Y4 may have all or some of the functions of the manufacture management apparatus X4 and the analyzer Y5. A server on a network (e.g., a cloud server) may also have some of the functions of the manufacture management apparatus X4 and the analyzer Y5.

Land-Based Inspection

As described above, inspection apparatuses known in the art inspect the positional deviation of a solder piece or a component (difference from its correct position) based on the design values obtained from computer-aided design (CAD) data. However, this method cannot yield reliable results when the actual land position deviates from the design value. To respond to this, the inspection apparatuses Y1 to Y3 according to the present embodiment analyze an image of an inspection target board to determine the actual land position, and measures and inspects the target using the actual land position as a reference. This method is herein referred to as a land-based inspection.

In each of the post-solder printing inspection, the post-mount inspection, and the post-reflow inspection, the land is hidden under the solder piece or the component. Correctly determining the position of the land from the appearance image is difficult in these processes. The method according to the present embodiment includes (1) preliminary learning the positional relationship between the elements on a sample board, and (2) determining the land position during the inspection process based on the positional relationship between the elements on a target board obtained from its image. More specifically, the position of an element that is not hidden under a solder piece or a component (e.g., a wiring pattern) is determined from an image, and then the position of a land is estimated based on its relative position to the element.

Specific examples of (1) learning the positional relationship and (2) determining the land position will now be described with reference to the drawings.

1. Positional Relationship Learning

Figure 2:
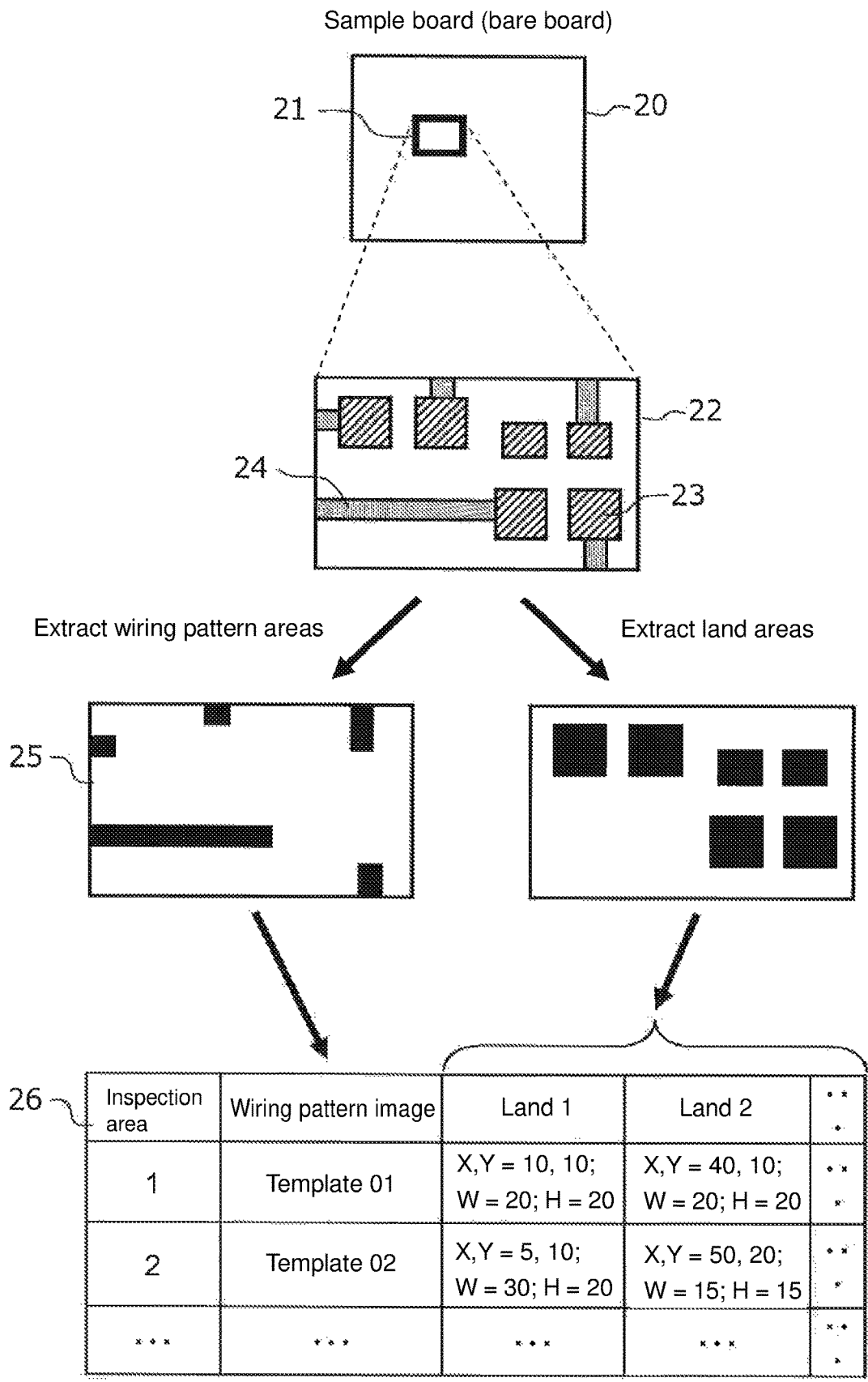
FIG. 2 is a diagram schematically describing a process for learning a positional relationship.

FIG. 2 is a diagram schematically describing the process for learning a positional relationship. This process is performed by, for example, the analyzer Y5 when generating an inspection program.

First, a sample board 20 is imaged. The sample board 20 may be a bare board with no solder printed or no component mounted (that is, a board having lands being entirely uncovered). The imaging may be performed using any one of the inspection apparatuses Y1 to Y3 or using another imaging apparatus. The inspection apparatuses Y1 to Y3 typically have a field of view smaller than the board size (e.g., the board has each side of 15 to 40 cm, whereas the field of view has each side of about 3 cm). A single board is thus divided into a plurality of small areas (inspection areas) for inspection. The positional relationship learning process is also performed for each inspection area during the inspection. An image 22 in FIG. 2 corresponds to an inspection area 21. The image 22 includes six lands 23 and five wiring patterns 24.

The analyzer Y5 then extracts the areas of the wiring patterns 24 from the image 22 based on the color of the wiring patterns 24 (e.g., green), and binarizes the patterns to generate a wiring pattern image 25. The wiring pattern image 25 is used as a template image in detecting wiring patterns (template matching), which is performed in determining a land position.

Figure 3A:
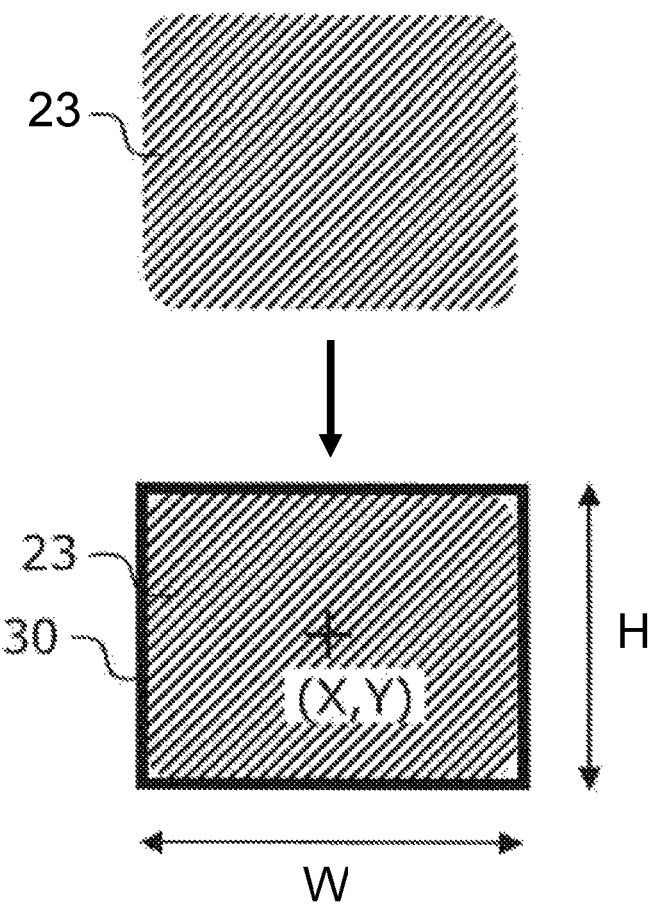
FIGS. 3A and 3B are diagrams describing a method for detecting the position and the size of a land.
Figure 3B:
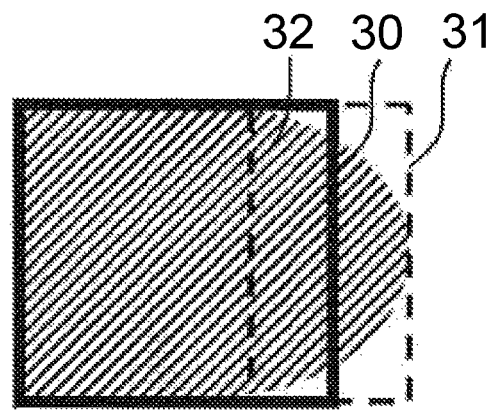

The analyzer Y5 also extracts the areas of the lands 23 from the image 22 based on the color of the lands 23 (e.g., copper foil color). The analyzer Y5 then calculates a land position (X, Y), a land width (W), and a land height (H) for each extracted land 23. As shown in FIG. 3A, for example, a rectangular frame 30 is fitted on the extracted area of the land 23 (hatched area), and the center of the rectangular frame 30 is defined as the land position (X, Y), the length of the rectangular frame 30 in X-direction is defined as the land width (W), and the length of the rectangular frame 30 in Y-direction is defined as the land height (H). For the land 23 having a curved edge, the rectangular frame 30 may be fitted to position in the middle between a circumscribed rectangle 31 and an inscribed rectangle 32 as shown in FIG. 3B. The land position (X, Y), the land width (W), and the land height (H) may be represented using, for example, coordinates defined in an image coordinate system having the upper left corner of the image as its origin.

Information about the wiring pattern image 25, the land position (X, Y), the land width (W), and the land height (H) is stored into a positional relationship information table 26 (FIG. 2). The processing described above is performed for each of all the inspection areas to enable learning of the relative positional relationship between the wiring patterns and the lands for each inspection area. The positional relationship information table 26 is incorporated in the inspection programs for the inspection apparatuses Y1 to Y3. The positional relationship between the wiring patterns and the lands in the sample board may not precisely match the positional relationship in the inspection target board due to individual differences between the boards or strains in the boards. However, such differences are negligible, because the field of view is sufficiently smaller than the board size.

2. Land Position Determination

Figure 4:
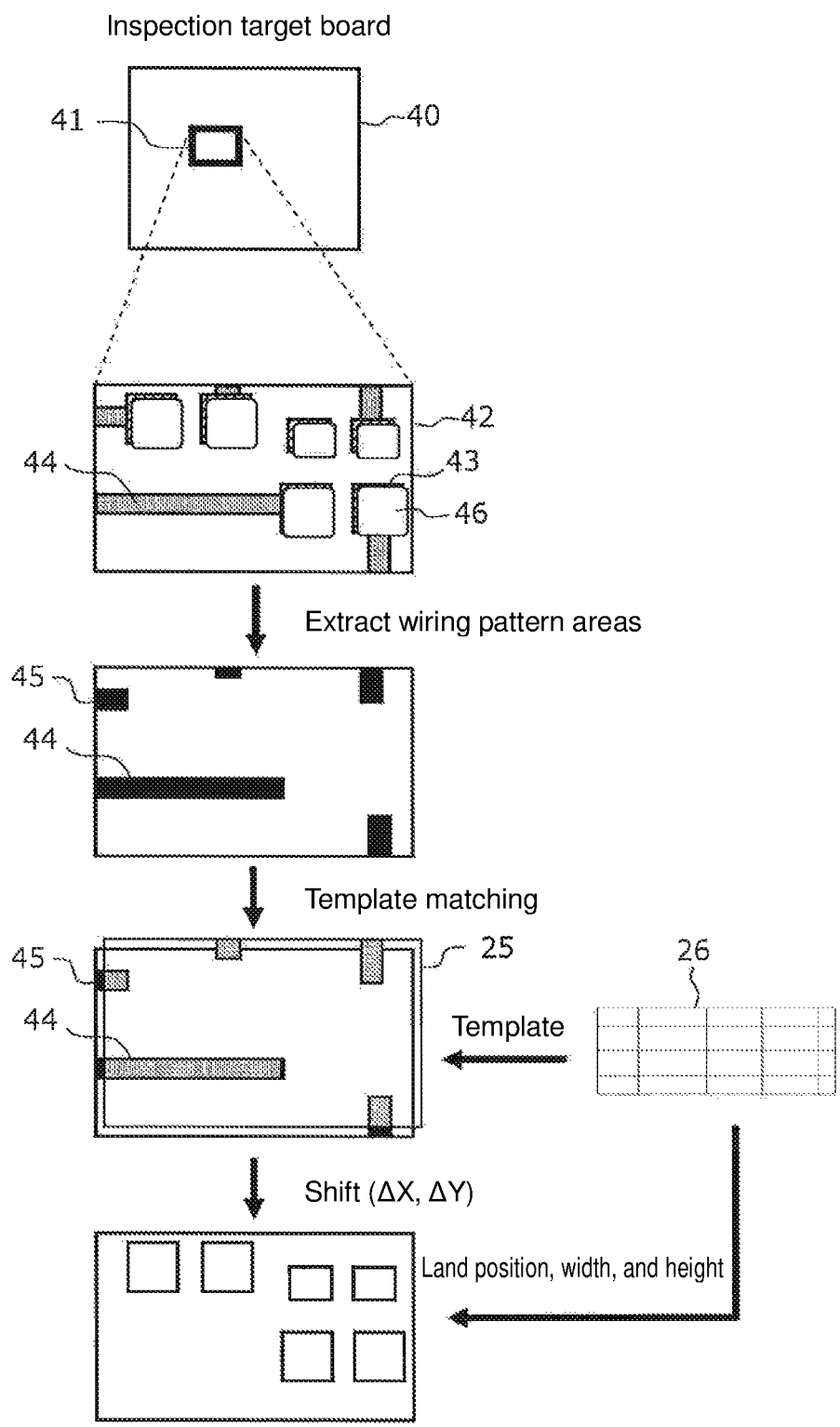
FIG. 4 is a diagram schematically describing a process for determining a land position.

FIG. 4 is a diagram schematically describing a process for determining a land position. This process is performed by the inspection apparatuses Y1 to Y3 during inspection. Although this process described below is performed in the post-solder printing inspection, basically the same process is performed both in the post-mount inspection and the post-reflow inspection.

First, an inspection target board 40 is imaged to capture an image 42 of an inspection area 41. The inspection area 41 corresponds to the inspection area 21 in FIG. 2. Unlike the sample board (refer to FIG. 2), the land 43 is mostly hidden under a solder piece 46. Thus, determining the position and the size of the land 43 directly from the image 42 is difficult.

The solder printing inspection apparatus Y1 extracts the areas of the wiring patterns 44 from the image 42 based on the color of the wiring patterns 44 (e.g., green), and binarizes the patterns to generate a wiring pattern image 45. The solder printing inspection apparatus Y1 obtains the wiring pattern image 25 corresponding to the inspection area 41 from the positional relationship information table 26. The solder printing inspection apparatus Y1 performs template matching using this image as a template to determine the positions of the wiring patterns 44 in the wiring pattern image 45. More specifically, the solder printing inspection apparatus Y1 evaluates the degree of matching between the template and the wiring pattern image 45 while shifting the template (wiring pattern image 25) pixel by pixel in X-direction and Y-direction to determine a maximum shift ($\Delta X$, $\Delta Y$) that allows the highest degree of matching. This operation of determining the maximum shift ($\Delta X$, $\Delta Y$) that allows the highest degree of matching corresponds to the operation of determining the positions of the wiring patterns 44.

The solder printing inspection apparatus Y1 then obtains information about the land position (X, Y), the land width (W), and the land height (H) corresponding to the inspection area 41 from the positional relationship information table 26. The solder printing inspection apparatus Y1 adds the shift ($\Delta X$, $\Delta Y$) to the land position (X, Y) to determine the land position in the image 42 (X+$\Delta X$, Y+$\Delta y$). The values of the land width (W) and the land height (H) are retained.

Through the processing described above, the land positions in the image are estimated using the positions of the elements other than the lands (e.g., wiring patterns). This allows highly accurate determination of the land positions for lands that may be hidden under solder pieces or under other components.

Structure of Inspection Apparatus

Figure 5:
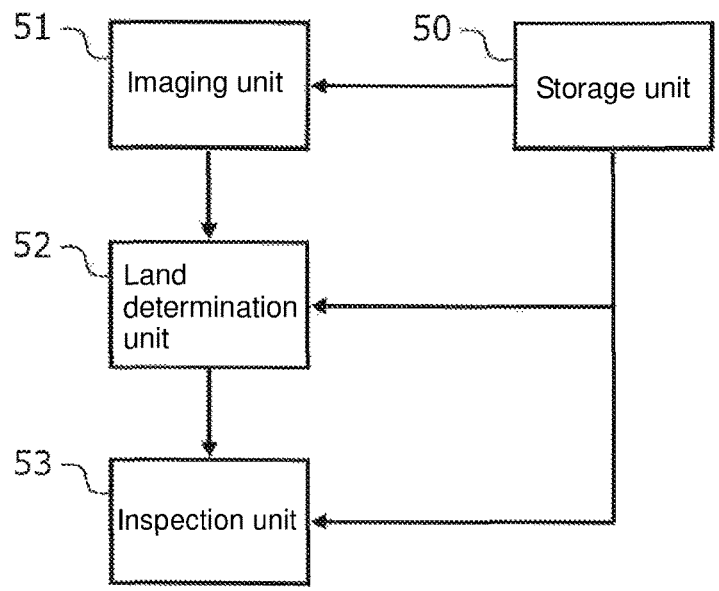
FIG. 5 is a functional block diagram of an inspection apparatus.

FIG. 5 is a block diagram schematically showing the functional units common to the inspection apparatuses Y1 to Y3. Each of the inspection apparatuses Y1 to Y3 mainly includes a storage unit 50, an imaging unit 51, a land determination unit 52, and an inspection unit 53. The storage unit 50 stores, for example, inspection programs defining the operation of the inspection apparatus and data obtained from inspection (e.g., measurement values and inspection results). The imaging unit 51 images an inspection target board to capture its image. The imaging unit 51 includes, for example, an imaging apparatus that can capture color images. The land determination unit 52 determines the position of a land. The inspection unit 53 inspects a solder piece or a component. These functions are implemented by the processor (CPU) in each of the inspection apparatuses Y1 to Y3 executing intended programs and controlling the storage device and the imaging apparatus.

Figure 6:
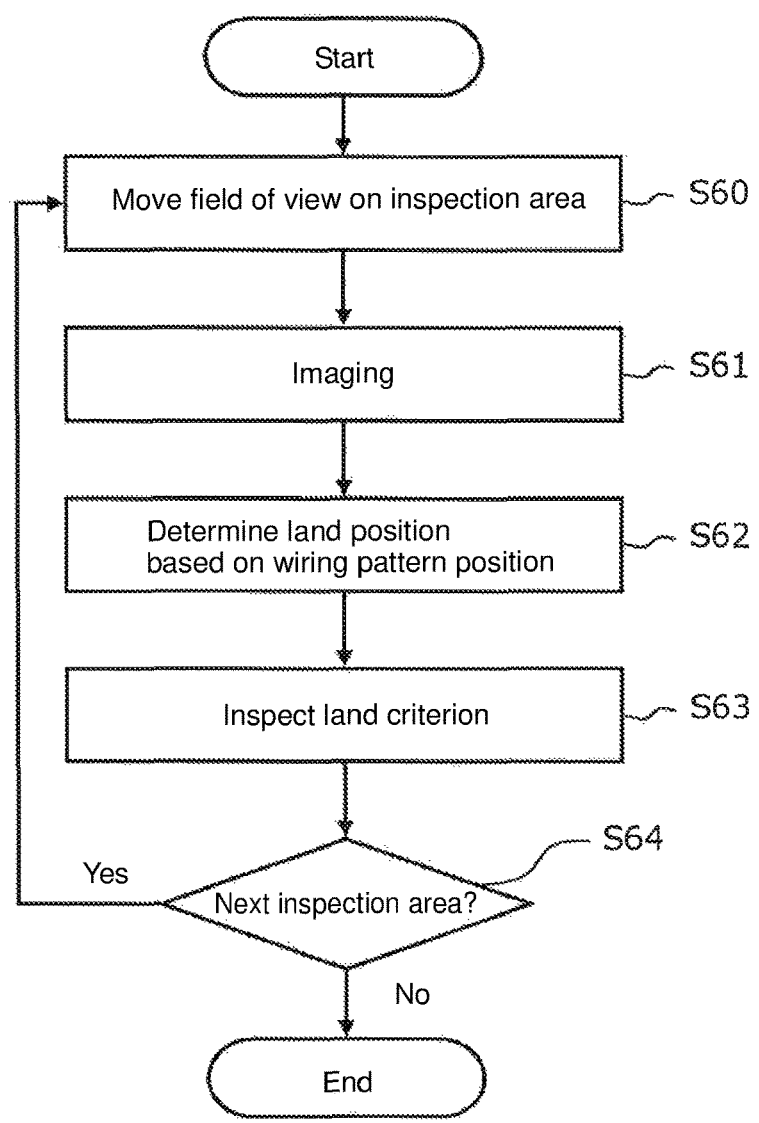
FIG. 6 is a flowchart showing the operation of the inspection apparatus.

FIG. 6 is a flowchart showing the operation of the inspection apparatuses Y1 to Y3. When each of the inspection apparatuses Y1 to Y3 receives an inspection target board, the imaging unit 51 reads an inspection program from the storage unit 50, and focuses its field of view on a first inspection area (step S60). The imaging unit 51 then captures an image of the inspection area (step S61). The land determination unit 52 determines the position of each land based on the positions of wiring patterns included in the image (step S62). The process for determining the land position is described in detail above with reference to FIG. 4. The inspection unit 53 then inspects the solder piece or the component on each land using the land position determined by the land determination unit 52 as a reference (step S63). When a plurality of inspection areas are defined, the processing in steps S60 to S63 is performed for each inspection area (step S64).

Items of Land-Based Inspection

Items of land-based inspection performed by the inspection unit 53 will now be described below. The items of land-based inspection are mere examples, and may be modified as appropriate in accordance with the specifications of the boards or the components, or the purpose of the inspection or the measurement.

Figure 7A:
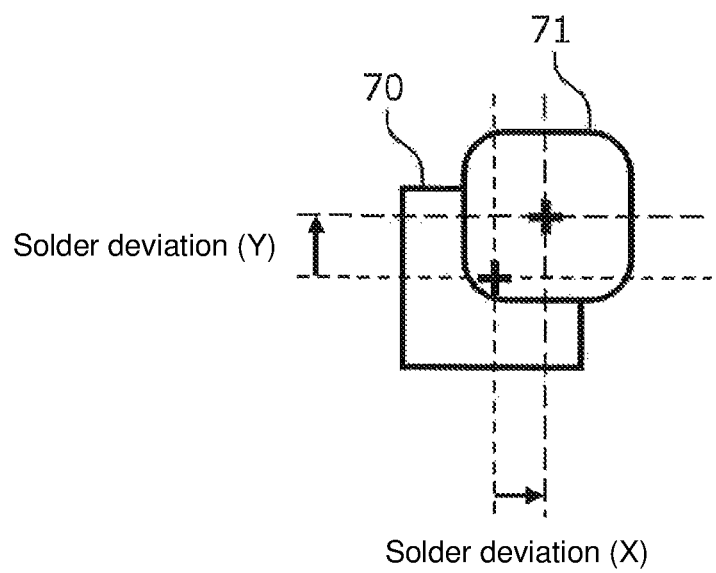
FIGS. 7A and 7B are diagrams showing examples of items for a land-based inspection.

FIG. 7A is a diagram showing an example of a solder deviation for each land measured in the post-solder printing inspection. The solder deviation for each land is a difference between the center of a land 70 and the center of a solder piece 71 printed on the land 70. The center of the solder piece 71 corresponds to the center of gravity of the solder area extracted from the image (when a single land includes a plurality of solder areas, the center of gravity of the solder area with the largest surface area or the largest volume may be used).

Figure 7B:
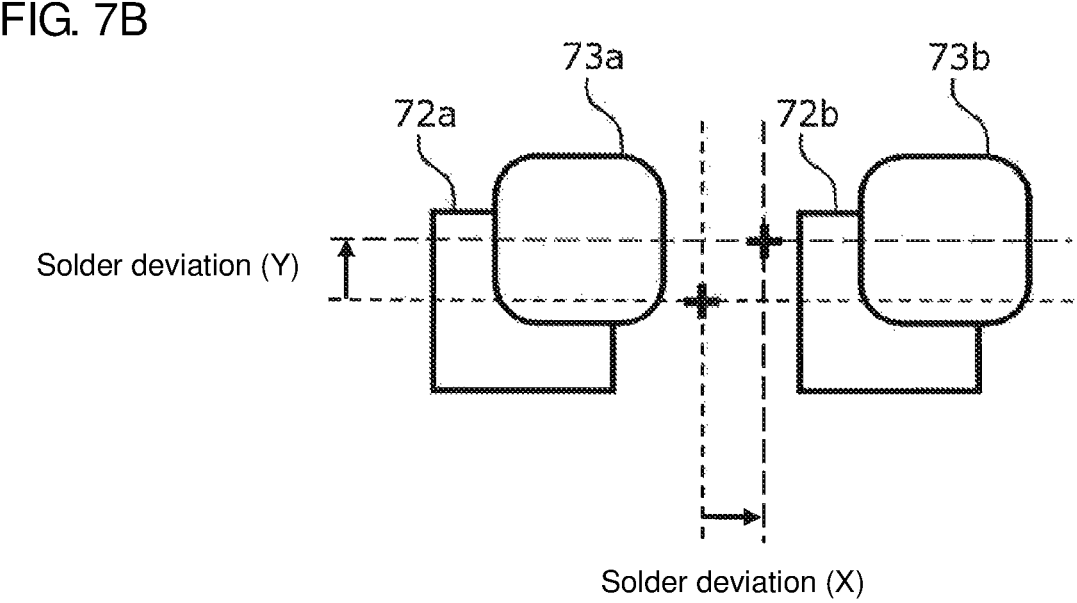

FIG. 7B is a diagram showing an example of a solder deviation for each component measured in the post-solder printing inspection. The solder deviation for each component is a difference between the center of a group of lands 72a and 72b, each of which corresponds to one of the electrodes included in the single component, and the center of a group of solder pieces 73a and 73b, each of which corresponds to one of the electrodes included in the single component. The center of the group of lands 72a and 72b may be defined as the center of gravity of the centers of all the lands 72a and 72b, or may be defined as the center of a circumscribed rectangle containing all the lands 72a and 72b. In the above first example, when the single component has two electrodes as shown in FIG. 7B, the corresponding two lands 72a and 72b each have the center (Xn, Yn) (n=1, 2). The center of the group of lands 72a and 72b is thus determined to be ((X1+X2)/2, (Y1+Y2)/2). The center of the group of solder pieces 73a and 73b may also be determined in the same manner as for the group of the lands.

Figure 8A:
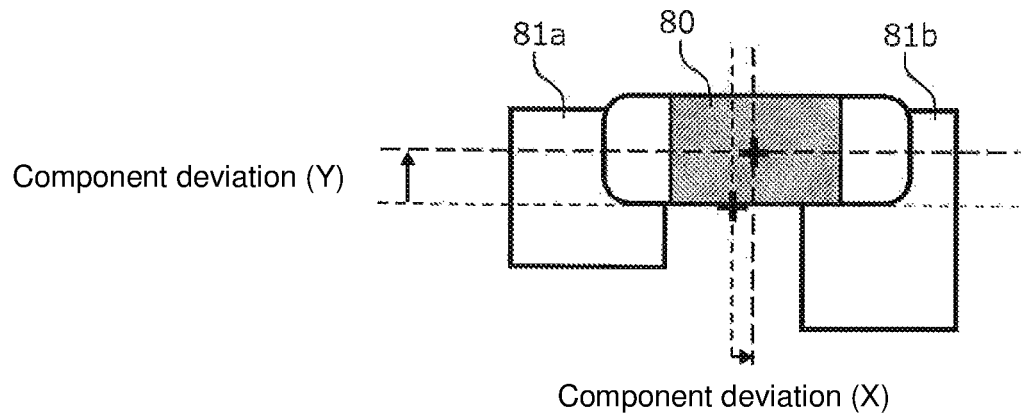
FIGS. 8A to 8C are diagrams showing examples of items for a land-based inspection.

FIG. 8A is a diagram showing an example of a component deviation measured in the post-mount inspection or the post-reflow inspection. The component deviation is a difference between the center of the component 80 and the center of a group of lands 81a and 81b, each of which corresponds to one of the electrodes included in the component 80. The center of the component 80 is defined as the center of gravity of the component area extracted from the image. The center of the group of the lands 81a and 81b may be determined in the same manner as in the example in FIG. 7B.

Figure 8B:
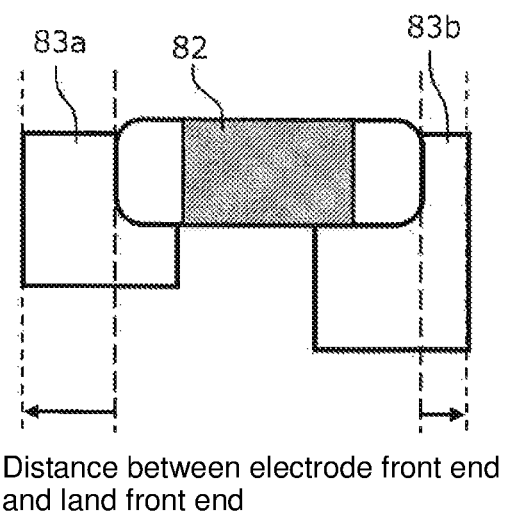

FIG. 8B is a diagram showing an example of a distance between a front end of an electrode and a front end of a land. The front end position of the electrode may be determined by detecting an edge of a component area 82 extracted from the image. The front end position of the land may be determined in accordance with the center of the land 83a or 83b, and its land width or its land height.

Figure 8C:
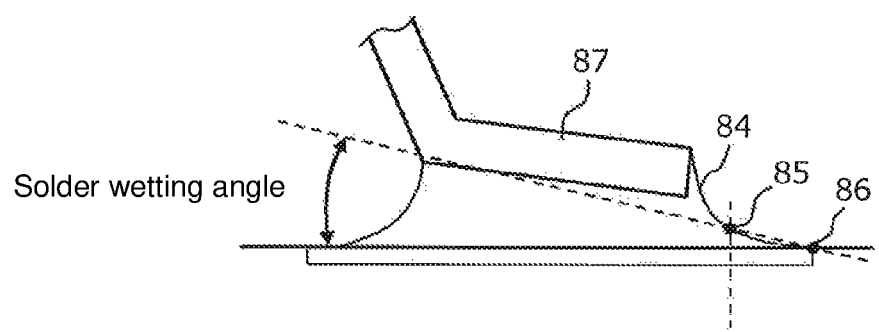

FIG. 8C is a diagram showing an example of a solder wetting angle at the front end of the electrode measured in the post-mount inspection or the post-reflow inspection. The solder wetting angle is an inclination of the skirt portion of a solder fillet 84. The solder wetting angle is defined in the present embodiment as an angle formed between the land surface and the line connecting the front end of the land 86 and a point 85 on the surface of the solder fillet 84 as shown in FIG. 8C. The point 85 is defined at a predetermined distance (e.g., 50 μm) inward from the front end of the land 86 toward an electrode 87.

The measurement values and the inspection results (quality determination results) obtained by the inspection apparatuses Y1 to Y3 are collected in the analyzer Y5 as inspection data. The analyzer Y5 stores the inspection data collected from the inspection apparatuses Y1 to Y3 into an inspection database shown in FIG. 9. In the example shown in FIG. 9, each component is managed in association with the inspection data obtained in the post-solder printing inspection, the post-mount inspection, and the post-reflow inspection. Each row of the table stores the inspection results of one component, including a board ID, an item number, a measurement value and an inspection result obtained in each process, and a result of visual inspection. Each inspection result is either pass (acceptable) or fail (defective). When the result is fail (defective), information about the type of the defect (inspection item) is also added.

Process Improvement Operation

A process improvement operation performed by the analyzer Y5 will now be described. The process improvement operation involves analyzing the cause of a defect or quality deterioration (defect sign) based on the inspection data collected from the inspection apparatuses Y1 to Y4, and providing feedback (FB) or feedforward (FF) to each of the manufacturing apparatuses X1 to X3 to remove the cause as appropriate.

Figures 10, 11:
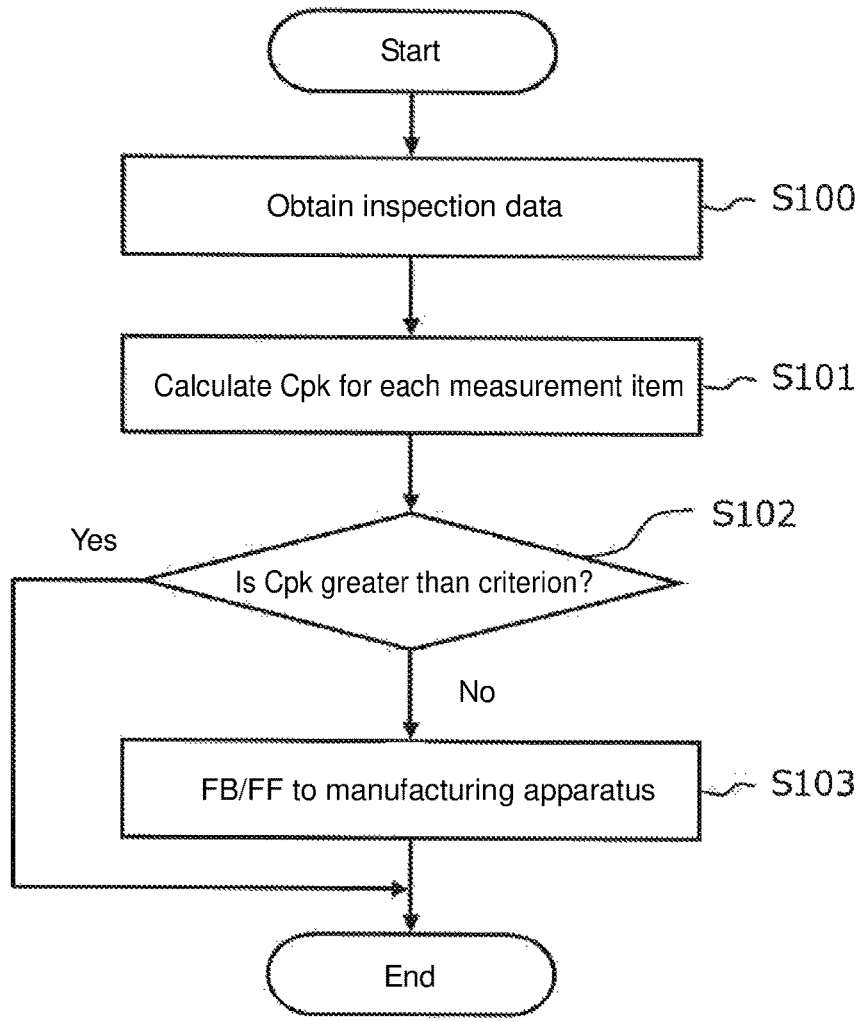
FIG. 10 is a flowchart showing a process improvement operation.
FIG. 11 is a diagram showing an example of mounting log data.

FIG. 10 is a flowchart showing the process improvement operation performed by the analyzer Y5 in one embodiment. This operation is triggered at predetermined intervals (e.g., once per hour or once per day), in predetermined cycles (e.g., every completion of M circuit boards), or when a predetermined event occurs (e.g., a defect, quality deterioration, a change in the manufacturing condition, a change in the lot, or a user instruction).

First, the analyzer Y5 reads inspection data to be analyzed from the inspection database (step S100). The analyzer Y5 may obtain all the data stored in the inspection database or may obtain selected data (e.g., data about a single circuit board, data about the latest N circuit boards, or data about circuit boards obtained during the preceding period T).

The analyzer Y5 then uses sets of inspection data obtained in step S100 to evaluate the variation in the values of each measurement item. More specifically, the analyzer Y5 calculates the process capability index (Cpk) for each measurement item (step S101). The process capability is the ability to produce products within predetermined specification limits. More specifically, the Cpk can be calculated using the formula below.

$$Cpk=Cpu=(\text{upper specification limit}-\text{mean})/3\sigma \text{ when only the upper specification limit is used.} \quad (1)$$

$$Cpk=Cpl=(\text{mean}-\text{lower specification limit})/3\sigma \text{ when only the lower specification limit is used.} \quad (2)$$

$$Cpk=\min(Cpu,Cpl) \text{ when both the upper and lower specification limits are used.} \quad (3)$$

The Cpk is assumed to be 0 when the Cpk is a negative value. In the above formulas, $\sigma$ is a standard deviation.

The Cp, or the value of (upper specification limit−lower specification limit)/6$\sigma$, may also be used in place of the Cpk. The upper specification limit and the lower specification limit are determined based on the quality standard. The specification limits for a component deviation can be determined to be, for example, the electrode width±½.

In the present embodiment, the Cpk is calculated for each of the three measurement items, or the component deviation in the post-reflow inspection, the distance between the front end of the electrode and the front end of the land in the post-reflow inspection, and the solder wetting angle at the front end of the electrode in the post-reflow inspection. The distance between the front end of the electrode and the front end of the land, and the solder wetting angle at the front end of the electrode may both vary depending on the orientation of a terminal. The Cpk is thus evaluated for each orientation of the terminal (or specifically for four groups of orientations, namely, the positive-X-direction, the negative-X-direction, the positive-Y-direction, and the negative-Y-direction).

The analyzer Y5 then determines whether the Cpk for each measurement item satisfies a predetermined criterion (e.g., 1.33) (step S102). When the Cpk does not satisfy the predetermined criterion, the analyzer Y5 provides feedback (FB) or feedforward (FF) to at least one of the manufacturing apparatuses X1 to X3 (step S103).

For example, when the Cpk is less than 1.33 for the component deviation in the post-reflow inspection, the component mounting position in the mounter X2 may be corrected. For the correction, the direction and the amount of possible deviations of the component are determined based on the inspection data. The component mounting position is then corrected in the direction opposite to the direction of the deviations by an amount determined based on a typical average deviation.

When the Cpk is also less than 1.33 for the distance between the front end of the electrode and the front end of the land in the post-reflow inspection, the component mounting position in the mounter X2 may be corrected. For this correction, whether the distance between the front end of the electrode and the front end of the land tends to be larger or smaller than the design value is determined based on the inspection data, and the component mounting position may be corrected in the direction in which the distance approaches the design value.

When the Cpk is also less than 1.33 for the solder wetting angle at the front end of the electrode in the post-reflow inspection, the component mounting position in the mounter X2 may be corrected. For this correction, whether the solder wetting angle tends to be larger or smaller than the design value is determined based on the inspection data. When the angle can be larger than the design value, the component mounting position is corrected in the direction in which the front end of the electrode will be away from the front end of the land. When the angle can be smaller than the design value, the component mounting position is corrected in the direction in which the front end of the electrode will be nearer the front end of the land.

The FB or FF may be provided in any of the following manners. The analyzer Y5 may directly correct the control parameter for each of the manufacturing apparatuses X1 to X3. The analyzer Y5 may transmit an instruction for correcting the control parameter to each of the manufacturing apparatuses X1 to X3 or to the manufacture management apparatus X4. The analyzer Y5 may provide correction information for the control parameter to a user to prompt the user to perform a correction operation.

Although the Cpk is evaluated for each measurement item to determine whether to provide FB or FF in the example of FIG. 10, the process improvement operation is not limited to this method. The process improvement operation may collectively evaluate the Cpk for multiple measurement items to determine whether to provide FB or FF. For example, the Cpk for the component deviation in the post-reflow inspection and the Cpk for the solder deviation in the post-solder printing inspection are evaluated separately. When the Cpk is less than 1.33 for the component deviation in the post-reflow inspection and is not less than 1.33 for the component deviation in the post-solder printing inspection, the cause of the deviation is determined to be in the component mounting process, and the component mounting position in the mounter X2 is corrected. When the Cpk is less than 1.33 for the component deviation in the post-reflow inspection and is also less than 1.33 for the solder deviation in the post-solder printing inspection, the component deviation is determined to be caused by the variation in the solder positions in the solder printing process. In this case, only the solder printing conditions in the solder printing apparatus X1 are corrected, without correcting the component mounting position. Collectively evaluating the Cpk values for multiple measurement items enables identification of the cause of any defect as well as removal of the cause as appropriate for improving the process.

The Cpk values for the measurement values and the inspection results of the components may also be evaluated collectively. For example, even with the Cpk of less than 1.33 for the component deviation in the post-reflow inspection, the component that does not satisfy the inspection criterion in any of the inspection items in the post-solder printing inspection (e.g., a solder deviation, a solder surface area, and a solder volume) is determined to have the cause of its defect in the solder printing process. In this case, only the solder printing conditions may be corrected, without correcting the component mounting position of target components.

Advantages of Present Embodiment

The quality control system according to the first embodiment determines land positions using the positions of elements other than the lands as a reference, and thus accurately determines the actual positions of lands that may be hidden under solder pieces or components. The quality control system then inspects the solder pieces or the components using the actual land positions as a reference, and thus allows more accurate determination than with techniques known in the art, and prevents false negatives for defective components, and improves the first pass yield. The quality control system can also accurately measure any deviation of the solder pieces or the components relative to the lands to effectively identify the cause of any defect or to accurately determine the manufacturing variation or the process capability. The quality control system also sets the monitoring criterion for evaluating quality deterioration (defect sign), and is expected to improve the monitoring accuracy. The analyzer Y5 further analyzes the cause of any defect or quality deterioration based on the inspection data using the actual land positions as a reference, and thus is expected to improve the analysis accuracy.

Further, the quality control system uses the positional relationship information table generated using the measurement values of the sample board. The quality control system thus more accurately determines the relative positional relationship between the wiring patterns and the lands despite any deviation between the actual land surface area or shape from the corresponding CAD data (design value).

The template matching used to determine the positions of the wiring patterns allows simple and highly accurate determination of the wiring patterns despite any variation in the shapes and the positions of the wiring patterns due to, for example, differences between individual boards.

Second Embodiment

In the process improvement operation according to the first embodiment described above, the analyzer Y5 estimates the cause of quality deterioration based on the inspection data, and directly or indirectly corrects the control parameters for the manufacturing apparatuses. However, identifying a defective part of the manufacturing apparatuses needs detailed information about the structure or the state of each manufacturing apparatus. The quality control system (the inspection apparatuses Y1 to Y4 and the analyzer Y5) alone may have difficulties in identifying the true cause of the defect or quality deterioration or determining the control parameters for the manufacturing apparatuses. In particular, when the vendor of the manufacturing apparatuses differs from the vendor of the quality control system, the quality control system alone may often be actually unable to obtain detailed internal apparatus information from the manufacturing apparatuses or to write control parameters into the manufacturing apparatuses.

In response to this, the analyzer Y5 in the second embodiment uses information and log data associated with the manufacturing apparatuses X1 to X3 obtained through the manufacture management apparatus X4 and the inspection data obtained from the inspection apparatuses Y1 to Y4 to analyze the cause of any defect or quality deterioration. The analyzer Y5 then provides the analysis results including information indicating a highly possible factor for the defect together with its supporting data to the manufacture management apparatus X4 or to the manufacturing apparatuses X1 to X3. The analysis results provided to the manufacturing apparatuses will assist the manufacturing apparatuses in identifying the cause and correcting the control parameters from their ends. The manufacturing apparatuses X1 to X3 can, for example, use those analysis results and the internal apparatus information to identify the cause of the defect or quality deterioration, or to automatically self-correct their control parameters.

Analysis Results

The analysis results provided by the analyzer Y5 to the manufacturing apparatuses may include, for example, any of the five items of information below.

a. Possible Cause of Defect or Quality Deterioration

A possible cause of a defect or quality deterioration refers to a highly possible factor among such factors associated with the manufacturing apparatuses. At least one possible cause is selected.

b. Supporting Value for Each Possible Cause

A supporting value is information serving as a basis for a highly possible cause. The supporting value is used to compare the possible cause with other factors not selected as the possible cause.

c. Information Identifying Location of Defect or Quality Deterioration

This information includes, for example, the occurrence time of any defect or quality deterioration, the board ID, and the location of the defect or quality deterioration, such as the mounting surface (front and/or back). The occurrence time of the defect or quality deterioration may be provided as the processed time in the manufacturing apparatuses. Using such information about the processed time in the manufacturing apparatuses, the manufacturing apparatuses can easily analyze the relationship between the defect or quality deterioration and an error occurring around the processed time, or between the defect or quality deterioration and the time at which the control parameters or materials are changed.

d. Operating Site of Possible Cause of Defect or Quality Deterioration

When, for example, a component included in one of the manufacturing apparatuses is a possible cause of a defect or quality deterioration, information about the manufacturing apparatus and the site of the apparatus where the component has been used is provided.

e. Current Operating Site of Possible Cause

When the operating site of the component can change, the information can be used readily to, for example, stop the use of the component that can cause the defect or quality deterioration, replace the component with another one, or perform maintenance.

Example Analysis Results Provided to the Mounter

Examples of the analysis results provided to the mounter X2, which is one of the manufacturing apparatuses, will now be described. The mounter X2 includes a head, a nozzle, a feeder, and other mechanical parts for mounting components. When these mechanical parts deteriorate or for example wear out, these mechanical parts can cause errors such as insufficient attraction of a component or a positional deviation of a component. The analyzer Y5 thus performs an analysis process described below when a defect associated with the component position occurs a predetermined number of times or when the defect rate exceeds a threshold in the post-reflow inspection.

First, the analyzer Y5 obtains mounting log data of the mounter X2 from the manufacture management apparatus X4. FIG. 11 shows an example of mounting log data. Each row of the table stores the mount records of one component, including a board ID, an item number, a nozzle number, a nozzle ID, a feeder ID, and a head ID. The analyzer Y5 uses the mounting log data to identify a mechanical part (a nozzle, a feeder, or a head) used to mount the component onto the circuit board. The nozzle ID, the feeder ID, and the head ID are used to identify the corresponding individual part. The nozzle number is used to specify the position where the nozzle is mounted on the mounter.

The analyzer Y5 then reads inspection data from the inspection database. The inspection data includes, as the inspection record for each component, a board ID, an item number, a measurement value and an inspection result obtained in each process, and a result of visual inspection (refer to FIG. 9).

The analyzer Y5 then counts the number of defects associated with the component position for each mechanical part (for each individual part) of the mounter X2 using the mounting log data and the inspection data. When each of the mechanical parts is mounted at a fixed position, the analyzer Y5 may count the number of defects for each mounting position instead for each individual part. A defect to be counted may exclusively be a defect that can be detected through visual inspection. For ease of explanation, detecting defects in the nozzle will now be described. The same applies to mechanical parts other than the nozzle.

The analyzer Y5 calculates four indices, namely, the number of defects, the defect rate, the odds ratio, and the lower limit of a 95% confidence interval for the odds ratio, as information for identifying a nozzle that can cause a defect. The number of defects is the count of defective components mounted using a certain nozzle. The defect rate is the ratio of the number of defective components to the total number of components mounted using a certain nozzle. The odds ratio is an index indicating the probability of defective components when the components are mounted using a certain nozzle. The 95% confidence interval for the odds ratio is the range in which the true odds ratio (the odds ratio obtained when the number of samples is sufficient) has a probability of 95%.

In one example, the mounter X2 includes three nozzles, or a nozzle N001, a nozzle N002, and a nozzle N003. The odds ratio and its 95% confidence interval for the nozzle N001 are calculated using the formula below, where a is the number of defective components mounted using the nozzle N001, b is the number of acceptable components mounted using the nozzle N001, c is the number of defective components mounted using the nozzles other than the nozzle N001 (the nozzle N002 or N003), and d is the number of acceptable components mounted using the nozzles other than the nozzle N001 (the nozzle N002 or N003).

$$\text{Odds ratio} = \frac{ad}{bc} \quad \text{Formula 1}$$

Upper limit of 95% confidence interval =

$$\exp\left[\ln\left(\frac{ad}{bc}\right) + 1.96 \times \sqrt{\left(\frac{1}{a} + \frac{1}{b} + \frac{1}{c} + \frac{1}{d}\right)}\right]$$

Lower limit of 95% confidence interval =

$$\exp\left[\ln\left(\frac{ad}{bc}\right) - 1.96 \times \sqrt{\left(\frac{1}{a} + \frac{1}{b} + \frac{1}{c} + \frac{1}{d}\right)}\right]$$

When the number of samples is small, the 95% confidence interval can deviate from the true value and produce incorrect results. Thus, the lower limit of the 95% confidence interval is to be used to indicate the probability of this nozzle causing the defect is at least greater than or equal to this lower limit.

The analyzer Y5 provides the analysis results including the above four indices associated with each nozzle to the mounter X2. The analyzer Y5 may also provide additional information about whether the nozzle is a highly possible cause of the defect for each nozzle. The values of the four indices can be used to determine whether the nozzle is a highly possible cause of the defect. When the odds ratio is greater than or equal to 3.0, for example, the nozzle is determined to be a possible cause of the defect. Multiple indices may also be used to determine the cause of the defect. For example, the nozzle may be determined to be a possible cause of the defect when the number of defective components is greater than or equal to 3 and the odds ratio is greater than or equal to 3.0.

FIG. 12 shows examples of the analysis results provided to the mounter X2. The nozzle ID and the possible cause correspond to the above information a. The number of defects, the defect rate, the odds ratio, and the lower limit of a 95% confidence interval for the odds ratio correspond to the above information b. These analysis results reveal that the nozzle N002 is a highly possible cause of the defect.

Although the processing described above is performed for a defect, similar processing can be performed for quality deterioration rather than a defect to yield and provide analysis results in the same manner. More specifically, the number of nearly defective components is counted instead of the number of defective components. For the measurement items associated with the component position (e.g., a component deviation), for example, a second inspection criterion stricter than the inspection criterion for determining whether the component is acceptable or defective may be defined. When a component has a measured value for the item falling within a range between the second criterion and the inspection criterion, the component may be determined to be a nearly defective component.

In this case as well, the information including the number of nearly defective components, the ratio of nearly defective components, the odds ratio, and the lower limit of a 95% confidence interval may be provided as analysis results in the same manner as shown in FIG. 12. In some embodiments, the information about the Cpk for the measurement items associated with the component position may be provided as analysis results in place of the odds ratio. For example, the analyzer Y5 calculates two indices, namely, the Cpk and its 95% confidence interval, for each nozzle. To avoid false positives, the upper limit of the 95% confidence interval for Cpk may be used. To avoid false negatives, the lower limit of the 95% confidence interval for Cpk may be used. When multiple measurement items are associated with the component position, the Cpk may be calculated for each measurement item and the measurement item with the smallest Cpk value may be used. When multiple components having different item numbers are mounted using the same single nozzle, the measurement values may be normalized to have the lower limit of 0 of the inspection criterion and the upper limit of 1 of the inspection criterion. After that, the Cpk may be calculated for the measurement values of all the components with different item numbers.

The 95% confidence interval for Cpk is calculated using the formula below.

Upper limit of 95% confidence interval = $\qquad$ Formula 2

$$Cpk + 1.96 \times \sqrt{\frac{Cpk^2}{2(N-1)} + \frac{1}{9N}}$$

-continued

Lower limit of 95% confidence interval =

$$Cpk - 1.96 \times \sqrt{\frac{Cpk^2}{2(N-1)} + \frac{1}{9N}}$$

The Cpk may be calculated for both the upper specification limit and the lower specification limit, and then the smaller Cpk value may be used. Similarly, the upper limit and the lower limit of the 95% confidence interval may be calculated using the Cpk for the upper specification limit and the Cpk for the lower specification limit, and then the smaller value may be used.

FIG. 13 shows examples of analysis results obtained using the Cpk. The nozzle ID and the possible cause correspond to the above information a. The Cpk and the lower limit of the 95% confidence interval for Cpk correspond to the above information b. In this case, whether the nozzle is a highly possible cause may be determined based on the Cpk and its 95% confidence interval. When, for example, the lower limit of the 95% confidence interval for Cpk is not more than 1.33, the nozzle may be determined to be a highly possible cause.

The analysis results for quality deterioration are promptly provided to the mounter X2 as described above when the quality deterioration occurs. This allows removal of the cause of the quality deterioration as appropriate before a defect actually occurs.

FIG. 14 shows examples of analysis results provided to the mounter X2. The defect location corresponds to the information c, the cause location corresponds to the information a, the operating site at defect occurrence corresponds to the information d, and the current operating site corresponds to the information e. These analysis results reveal that a defect occurred on the surface of the board B001, the date and the time when the mounter mounted the component is 10:23:36 on Jun. 30, 2016, the nozzle N001 is a highly possible cause of the defect, the nozzle N001 has been mounted on the nozzle 12 of the mounter MNT-0002 in the line SMT5 at the defect occurrence, and the nozzle N001 is currently on the nozzle 16 of the mounter MNT-0001 in the other line SMT3.

Advantages of Present Embodiment

The structure according to the second embodiment provides the analysis results of any defect or quality deterioration detected by the inspection apparatuses to the manufacturing apparatuses, and the manufacturing apparatuses can easily identify the cause of the defect and remove the cause as appropriate. This structure thus reduces defects and improves the quality. In particular, the quality control system according to the present embodiment yields the analysis results using the inspection data based on the actual land positions as a reference. The quality control system can thus provide useful and reliable information to the manufacturing apparatuses.

Third Embodiment

The first and the second embodiments describe the operation in which the analyzer Y5 improves the processes performed by each manufacturing apparatus using inspection data. The third embodiment describes an operation in which the analyzer Y5 optimizes the inspection criterion for each inspection apparatus using inspection data. The inspection criterion refers to a determination criterion (e.g., a threshold) for determining whether the inspection target is acceptable or defective for each item of inspection. An inspection criterion that is too loose increases false negatives for defective components, whereas an inspection criterion that is too strict lowers the first pass yield. The inspection criterion may thus be set as appropriate.

The inspection criterion used in the post-solder printing inspection or the post-mount inspection is typically set for each process. However, for example, a slight positional deviation of a solder piece or a component in the solder printing process or the mounting process may not always cause a defective solder joint after the reflow process. To properly detect only deviations that can cause defects in the post-reflow inspection (final inspection), the inspection criterion is to be set appropriately for each of the post-solder printing inspection and the post-mount inspection (these inspections are referred to as intermediate inspections).

The analyzer Y5 in the present embodiment sets the inspection criterion for such intermediate inspections to appropriate values to reflect the quality determination results in the final inspection using inspection data stored in the inspection database. Setting the criterion to appropriate values refers to changing (adjusting) the inspection criterion value for these intermediate inspections to increase the degree of agreement between the quality determination results in the final inspection and the quality determination results in the intermediate inspections.

A process for optimizing an inspection criterion performed by the analyzer Y5 will now be described using an example in which the solder printing inspection apparatus Y1 uses the inspection criterion to determine the quality of acceptable solder deviations.

Example Processing 1

The analyzer Y5 first reads inspection data (refer to FIG. 9) for components of the same type (components with the same item number) from the inspection database. The analyzer Y5 may obtain all the data stored in the inspection database or may obtain selected data (e.g., data about the latest N circuit boards, or data about circuit boards obtained during the preceding period T). The analyzer Y5 then classifies the read inspection data into acceptable component inspection data and defective component inspection data based on the final results of the post-reflow inspection or the visual inspection. The analyzer Y5 then calculates the distribution of solder deviation values measured in the post-solder printing inspection using the acceptable component inspection data (acceptable component distribution), and the distribution of solder deviation values measured in the post-solder printing inspection using the defective component inspection data (defective component distribution). The analyzer Y5 then calculates a most appropriate solder deviation value that can separate the acceptable component distribution and the defective component distribution, and sets the value as the inspection criterion for solder deviations in the post-solder printing inspection.

Example Processing 2

The above example processing 1 may not achieve sufficient accuracy when the defective component inspection data includes an insufficient number of samples. The correlation between first measurement values obtained in an intermediate inspection (e.g., solder deviations in the post-solder printing inspection) and second measurement values obtained in the final inspection (e.g., component deviations in the post-reflow inspection) is used to estimate the distribution of the second measurement values corresponding to the distribution of the first measurement values. The estimated group of samples may then be used to set the inspection criterion for the first measurement values to agree best with the quality determination results based on the second measurement values. A specific algorithm used in example processing 2 may be an algorithm described in Japanese Unexamined Patent Application Publication No. 2012-151251.

Although the inspection criterion for solder deviations is described in the present embodiment, the inspection criterion for other inspection items may be set in the same manner. Further, the inspection criterion used in the post-mount inspection or the post-reflow inspection may also be set in the same manner, in addition to the inspection criterion used in the post-solder printing inspection. The analyzer Y5 may set the inspection criterion by directly correcting the inspection criterion (an inspection program) of each of the inspection apparatuses Y1 to Y4, transmitting an instruction for correcting the inspection criterion to each of the inspection apparatuses Y1 to Y4, or providing correction information for the inspection criterion to a user to prompt the user to perform a correction operation.

Advantages of Present Embodiment

The structure according to the third embodiment allows the inspection criterion for the intermediate inspections to be changed to appropriate values based on the determination results in the final inspection. This can minimize erroneous determinations of components that would not be defective after the reflow process as defective in the post-solder printing inspection or in the post-mount inspection (false positives), or minimize erroneous determinations of components that would be defective after the reflow process as acceptable in the post-solder printing inspection or in the post-mount inspection (false negatives), and can reduce ineffective inspections. In particular, the quality control system according to the present embodiment performs inspection using the actual land positions as a reference, and optimizes the inspection criterion based on data obtained from the inspection. The quality control system is thus expected to enable more accurate and more reliable inspection.

Fourth Embodiment

The fourth embodiment enables the function of comparing the quality of an inspection item before and after the operating conditions of the manufacturing apparatuses X1 to X3 or the operating conditions of the inspection apparatuses Y1 to Y4 are changed. This allows easy verification of the influence (effects) of any change in the control parameters for the manufacturing apparatuses X1 to X3 or in the inspection criteria for the inspection apparatuses Y1 to Y4 based on the analysis results of the inspection data as described in the first to the third embodiments on the manufacturing quality or the inspection ability.

1. When the Control Parameters for Manufacturing Apparatuses are Changed

For example, the analyzer Y5 identifies the time (a change point) at which the control parameters (e.g., solder printing conditions or mounting conditions) are changed by referring to, for example, the information and the log data of the manufacturing apparatuses X1 to X3 obtained through the manufacture management apparatus X4. The analyzer Y5 then reads the inspection data from the inspection database and classifies the data into inspection data before the control parameters are changed and inspection data after the control parameters are changed. The analyzer Y5 then calculates the quality index (e.g., Cpk) for the intended measurement values (e.g., component deviations after the reflow process or solder wetting-up heights) for both before and after the change.

Figure 15:
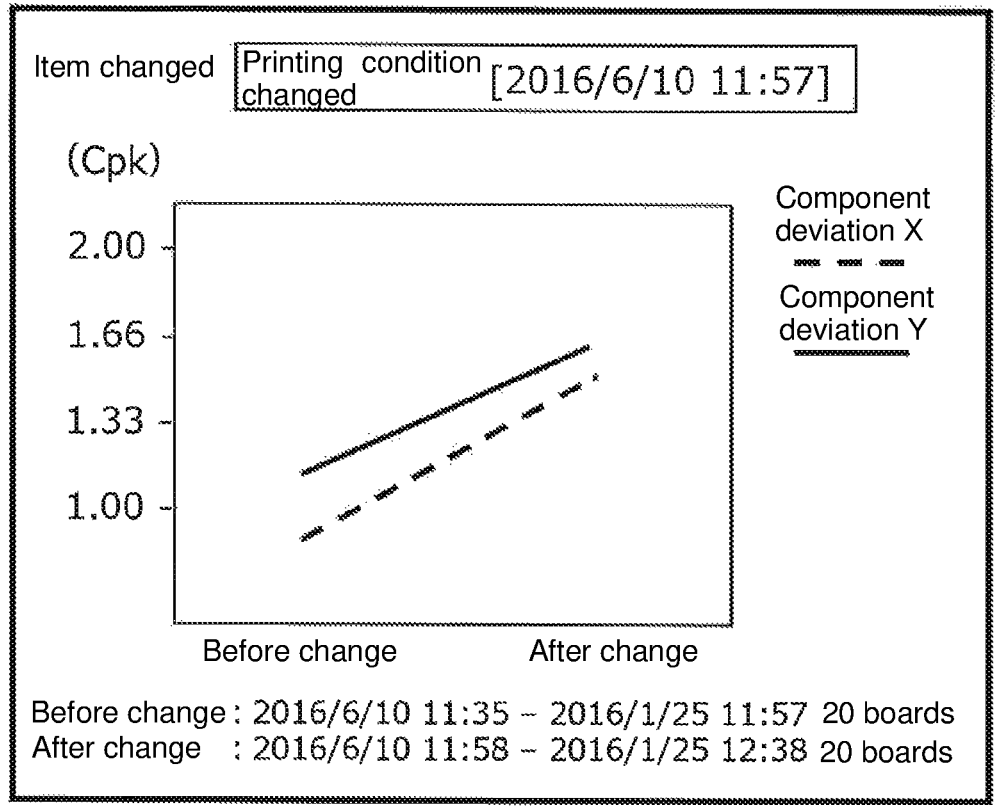
FIG. 15 is a graph showing comparison between the qualities before and after a printing condition is changed.

FIG. 15 shows an example screen displaying the results of comparison between the qualities before and after the change. The screen displays a graph showing the Cpk for the component deviations in 20 circuit boards produced before the solder printing conditions are changed and the Cpk for the component deviations in the 20 circuit boards produced after the solder printing conditions are changed. The component deviation in X-direction and the component deviation in Y-direction are both improved after the solder printing conditions are changed.

2. When the Monitoring Criterion for Inspection Apparatuses is Changed

The monitoring criterion is used to determine whether an abnormality has occurred in the process. The criteria are set for a quality index (e.g., the first pass yield or the Cpk) calculated using measurement values for multiple circuit boards and components.

For example, the analyzer Y5 identifies the time (a change point) at which the monitoring criterion for solder printing inspection apparatus Y1 or for the component inspection apparatus Y2 is changed by referring to, for example, the log data of the inspection apparatuses. The analyzer Y5 then reads the inspection data from the inspection database and classifies the data into inspection data before the monitoring criterion is changed and inspection data after the monitoring criterion is changed to calculate the quality index for both before and after the change. The quality index may be, for example, the Cpk for measurement values after the post-reflow inspection (e.g., component deviations or solder wetting-up heights), the false positive rate or the first pass yield in the post-reflow inspection, or the average cycle time (the change in productivity caused by the difference in the frequency of warning).

Figure 16:
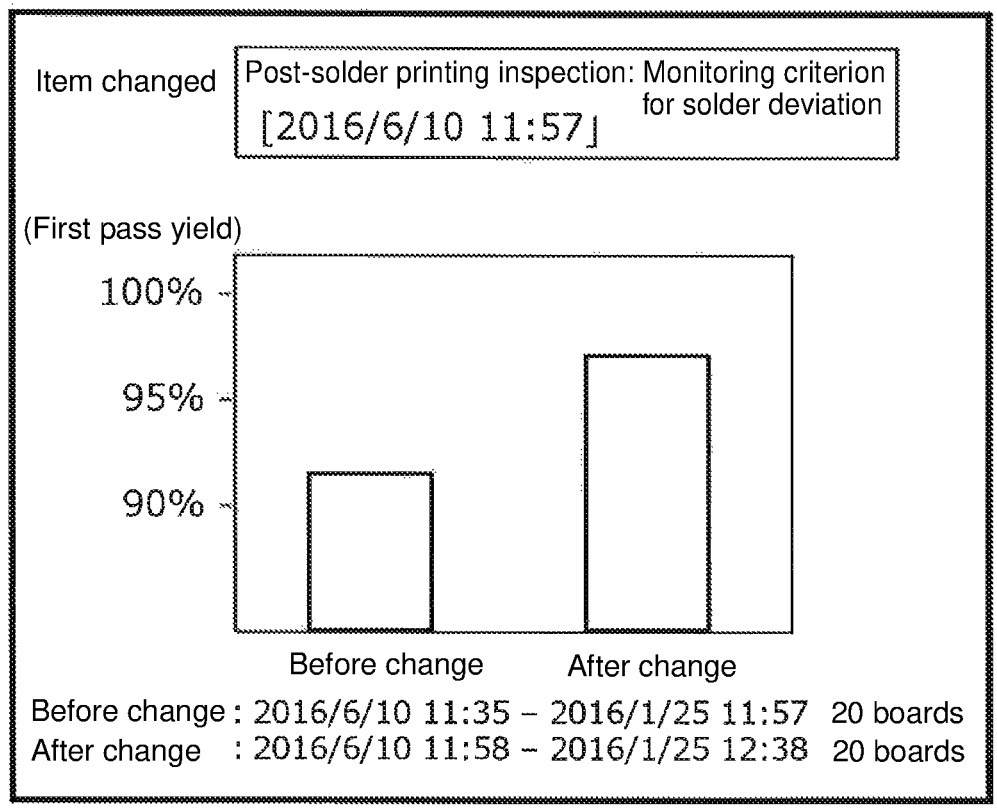
FIG. 16 is a graph showing comparison between the qualities before and after a monitoring criterion for solder deviations is changed.

FIG. 16 shows an example screen displaying the results of comparison between the qualities before and after the change. The screen displays a bar graph showing the change in the first pass yield in the post-reflow inspection when the monitoring criterion for solder deviations is changed in the post-solder printing inspection. The first pass yield is improved after the monitoring criterion is changed.

3. When the Inspection Criterion for Inspection Apparatuses is Changed

For example, the analyzer Y5 identifies the time (a change point) at which the inspection criterion for the solder printing inspection apparatus Y1 or for the component inspection apparatus Y2 is changed by referring to, for example, the log data of the inspection apparatuses. The analyzer Y5 then reads the inspection data from the inspection database and classifies the data into inspection data before the inspection criterion is changed and inspection data after the inspection criterion is changed to calculate the quality index for both before and after the change. The quality index may be, for example, the false positive rate or the first pass yield in the inspection apparatus with the changed inspection criterion, the false positive rate or the first pass yield in the post-reflow inspection, the actual defective rate in the visual inspection, or the average cycle time (change in productivity caused by the difference in the frequency of quality determination).

Figure 17:
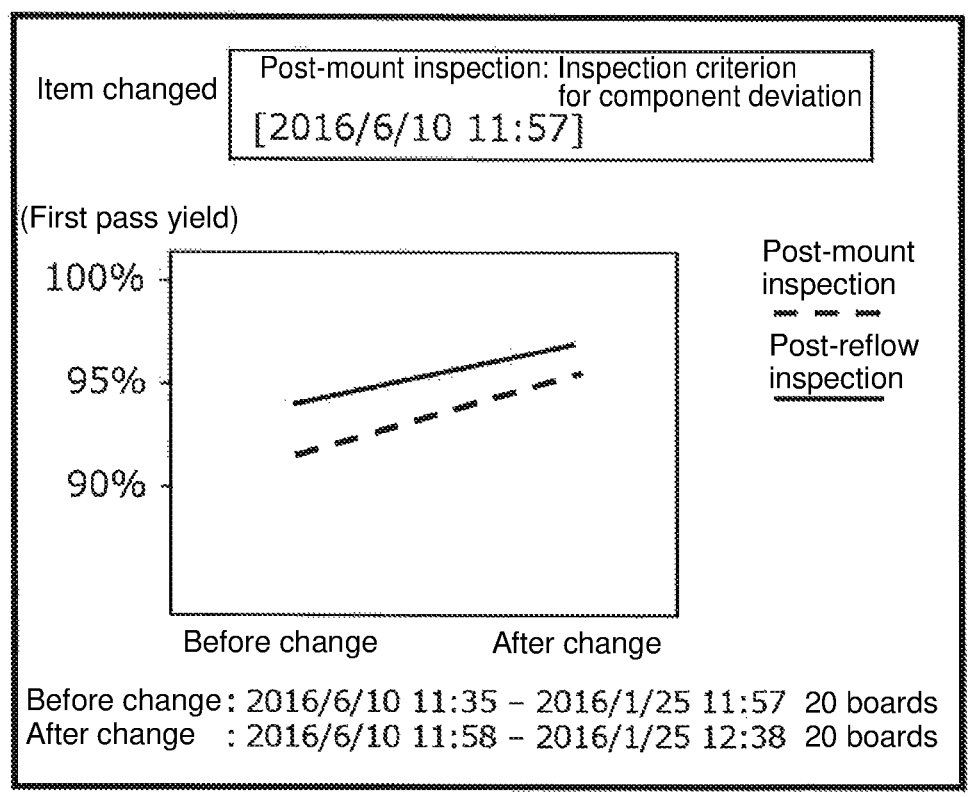
FIG. 17 is a graph showing comparison between the qualities before and after an inspection criterion for component deviations is changed.

FIG. 17 shows an example screen displaying the results of comparison between the qualities before and after the change. The screen displays a graph showing the change in the first pass yield in the post-mount inspection and the change in the first pass yield in the post-reflow inspection when the inspection criterion for component deviations is changed in the post-mount inspection. The quality is improved after the inspection criterion is changed.

Advantages of Present Embodiment

The structure according to the fourth embodiment allows easy and objective verification of the effects of any change in the operating conditions of the manufacturing apparatuses and/or the inspection apparatuses on the quality improvement. This can simplify the quality control of a surface mounting line and improve productivity.

REFERENCE SIGNS LIST

X1 solder printing apparatus
X2 mounter
X3 reflow furnace
X4 manufacture management apparatus
Y1 solder printing inspection apparatus
Y2 component inspection apparatus
Y3 appearance inspection apparatus
Y4 X-ray inspection apparatus
Y5 analyzer
20 sample board
21 inspection area
22 image
23 land
24 wiring pattern
25 wiring pattern image
26 positional relationship information table
40 circuit board
41 inspection area
42 image
43 land
44 wiring pattern
45 wiring pattern image
50 storage unit
51 imaging unit
52 land determination unit
53 inspection unit

The invention claimed is:
1. A quality control system, comprising:
a first inspection apparatus configured to perform an intermediate inspection for a board having a land on which a solder piece has been printed, or for the board having a component mounted on the solder piece;
a second inspection apparatus configured to perform a final inspection for inspecting the board having the component soldered to the land; and
an analyzer, wherein
each of the first and second inspection apparatuses, for a surface mounting line, comprises a processor configured with a program to perform operations comprising:
operation as an imaging unit configured to capture: an image of the board comprising the land on which the solder piece has been printed;
an image of the board comprising a component mounted on the solder piece; or
an image of the board comprising the component soldered to the land;
operation as a land determination unit configured to:
determine a position of an element on the board other than the land from the image of the board captured by the imaging unit, wherein the element comprises a wiring pattern formed on the board;
generate a pattern image by extracting an image of the element from the image of the board; and determine a position of the land included in the image based on the pattern image and the determined position of the element; and operation as an inspection unit configured to inspect the solder piece or the component on the land using the position of the land determined by the land determination unit as a reference, the inspection unit included in each of the first and second inspection apparatuses stores a value measured using the position determined by the land determination unit as a reference with an inspection criterion to determine whether an inspection target is acceptable or defective, and the analyzer comprises a second processor configured with a second program to perform operations comprising changing a value of the inspection criterion used in the intermediate inspection based on a result of the determination performed in the final inspection.

2. The inspection apparatus according to claim 1, wherein the element comprises a wiring pattern formed on the board.

3. The inspection apparatus according to claim 1, wherein the processor is configured with the program such that:

operation as the land determination unit comprises operation as the land determination unit that estimates the position of the land in the image based on positional relationship information defining a relative positional relationship between the element and the land, and the position of the element determined from the image, and the positional relationship information is information generated by measuring a sample board on which no solder piece has been printed.

4. The inspection apparatus according to claim 3, wherein the positional relationship information comprises a template of the element generated from an image of the sample board, and the processor is configured with the program such that operation as the land determination unit comprises operation as the land determination unit that determines the position of the element in the image of the board by template matching using the template.

5. A quality control system, comprising:

the inspection apparatus according to claim 1, and a second processor configured with a second program to perform operations comprising operation as an analyzer configured to analyze a cause of a defect or quality deterioration based on inspection data obtained by the inspection apparatus.

6. The quality control system according to claim 5, wherein the second processor is configured with the second program such that operation as the analyzer comprises operation as the analyzer that corrects a control parameter for a manufacturing apparatus included in the surface mounting line based on an analysis result of the cause of the defect or the quality deterioration.

7. The quality control system according to claim 6, wherein the second processor is configured with the second program such that operation as the analyzer comprises operation as the analyzer that provides the analysis result of the cause of the defect or the quality deterioration to the manufacturing apparatus included in the surface mounting line.

8. The quality control system according to claim 1, wherein the second processor is configured with the second program such that operation as the analyzer comprises operation as the analyzer that changes the value of the inspection criterion used in the intermediate inspection to increase a degree of agreement between the result of the determination performed in the final inspection and a result of the determination performed in the intermediate inspection.

9. The quality control system according to claim 5, wherein the second processor is configured with the second program such that, in response to an operating condition of a manufacturing apparatus or the inspection apparatus included in the surface mounting line being changed, operation as the analyzer comprises operation as the analyzer that generates and outputs information indicating a change in quality before and after the operating condition is changed.

10. A method for controlling an inspection apparatus for a surface mounting line, the method comprising: performing an intermediate inspection for a board having a land on which a solder piece has been printed, or for the board having a component mounted to the solder piece; and performing a final inspection for inspecting the board having the component soldered to the land, wherein each of performing the intermediate inspection and performing the final inspection comprise:

capturing: an image of the board comprising the land on which the solder piece has been printed; an image of the board comprising the component mounted on the solder piece; or an image of the board comprising the component soldered to the land;

determining a position of an element on the board other than the land from the captured image of the board, wherein the element comprises a wiring pattern formed on the board;

generating a pattern image by extracting an image of the element from the image of the board;

determining a position of the land included in the image based on the pattern image and the determined position of the element;

inspecting the solder piece or the component on the land using the determined position of the land as a reference;

measuring a value based on the determined position of the land and using the measured value as a reference with an inspection criterion to determine whether an inspection target is acceptable or defective; and changing a value of the inspection criterion used in the intermediate inspection based on a result of the determination performed in the final inspection.

11. A non-transitory computer-readable storage medium storing a program causing a processor to perform operations comprising the steps included in the method for controlling the inspection apparatus according to claim 10.

12. The method according to claim 10, wherein the element on the board comprises a wiring pattern formed on the board.

13. The method according to claim 10, further comprising measuring a sample board on which no solder piece has been printed to determine positional relationship information defining a relative positional relationship between the element and the land, wherein determining the position of the land included in the image comprises estimating the position of the land included in the image based on the positional relationship information and the position of the element determined from the image.

14. The method according to claim 13, wherein determining the position of the element on the board comprises template matching using a template generated from an image of the sample board.

15. The method according to claim 10, further comprising analyzing a cause of a defect or quality deterioration based on inspection data obtained by inspecting the solder piece or the component on the land.

16. The method according to claim 15, further comprising providing an analysis result of the cause of the defect or the quality deterioration.

17. The method according to claim 16, further comprising correcting a control parameter for a manufacturing apparatus based on the analysis result.

* * * * *